(12) United States Patent
Pinto

(10) Patent No.: US 6,407,256 B1
(45) Date of Patent: Jun. 18, 2002

(54) CYANO-PYRROLE, CYANO-IMIDAZOLE, CYANO-PYRAZOLE, AND CYANO-TRIAZOLE COMPOUNDS AS FACTOR XA INHIBITORS

(76) Inventor: Donald J. P. Pinto, 425 Brentford Rd., Kennett Square, PA (US) 19348

( * ) Notice: Subject to any disclaimer, the term of this patent is extended or adjusted under 35 U.S.C. 154(b) by 0 days.

(21) Appl. No.: 09/686,382

(22) Filed: Oct. 11, 2000

Related U.S. Application Data

(60) Provisional application No. 60/163,268, filed on Nov. 3, 1999.

(51) Int. Cl.⁷ .................... A07D 403/02; A61K 31/415
(52) U.S. Cl. ..................... 548/314.7; 514/406
(58) Field of Search ................. 548/314.7; 514/400

(56) References Cited

FOREIGN PATENT DOCUMENTS

| WO | WO 98/28269 | 7/1998 |
|----|-------------|--------|
| WO | WO 98/57937 | 12/1998 |
| WO | WO 98/57951 | 12/1998 |
| WO | WO 99/32454 | 7/1999 |

*Primary Examiner*—Floyd D. Higel
*Assistant Examiner*—Golam M. M. Shameem
(74) *Attorney, Agent, or Firm*—David H. Vance

(57) ABSTRACT

The present application describes inhibitors of factor Xa which are cyano-pyrazole, cyano-triazole, cyano-imidazole, and cyano-pyrrole compounds of Formulae Ia, Ib, Ic, and Id:

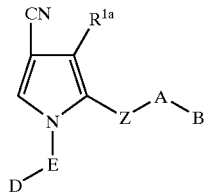

Ia

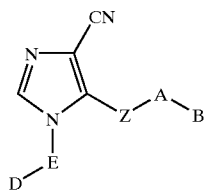

Ib

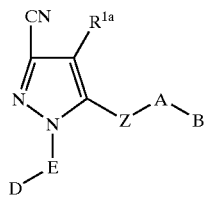

Ic

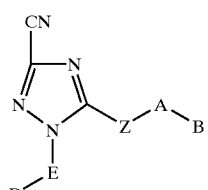

Id or pharmaceutically acceptable salt forms thereof.

15 Claims, No Drawings

CYANO-PYRROLE, CYANO-IMIDAZOLE, CYANO-PYRAZOLE, AND CYANO-TRIAZOLE COMPOUNDS AS FACTOR XA INHIBITORS

This application claims benefit of No. 60/163,268 Nov. 3, 1999.

FIELD OF THE INVENTION

This invention relates generally to cyano-pyrrole, cyano-imidazole, cyano-pyrazole, and cyano-triazole compounds which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

Inhibition of factor Xa may be more efficient than inactivation of thrombin in interrupting the blood coagulation system. Therefore, efficacious and specific inhibitors of factor Xa are needed as potentially valuable therapeutic agents for the treatment of thromboembolic disorders. It is thus desirable to discover new factor Xa inhibitors.

WO98/28269 describes factor Xa inhibitors of the formula:

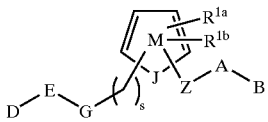

wherein ring M can be a variety of N-containing heterocycles including pyrrole, pyrazole, imidazole, and triazole and D is substituted meta or para to G on E. However, WO98/28269 does not disclose cyano-substituted compounds like those of the present invention.

WO98/57951 describes factor Xa inhibitors of the formula:

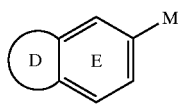

wherein ring D is selected from —CH$_2$N═CH—, —CH$_2$CH$_2$N═CH—, a 5–6 membered aromatic system containing from 0–2 heteroatoms selected from the group N, O, and S, ring E contains 0–2 N atom and M is a variety of rings including pyrrole, pyrazole, imidazole, and triazole. WO98/57951 does not, however, disclose cyano-substituted compounds like those of the present invention.

WO98/57937 describes factor Xa inhibitors of the formula:

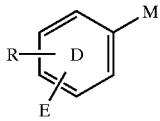

wherein ring D is phenyl or pyridyl and M is a variety of rings including pyrrole, pyrazole, imidazole, and triazole. However, WO98/57937 does not disclose cyano-substituted compounds like those of the present invention.

PCT/US98/26427 describes factor Xa inhibitors of the formula:

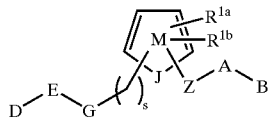

wherein ring M is a variety of rings including pyrrole, pyrazole, imidazole, and triazole and D is substituted ortho to G on E. However, PCT/US98/26427 does not disclose cyano-substituted compounds like those of the present invention.

SUMMARY OF THE INVENTION

One object of the present invention is to provide novel cyano-pyrazole and cyano-triazole compounds which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel compounds for use in therapy.

It is another object of the present invention to provide the use of novel compounds for the manufacture of a medicament for the treatment of a thromboembolic disorder.

These and other objects, which will become apparent during the following detailed description, have been achieved by the inventors' discovery that compounds of formulae Ia, Ib, Ic, and Id:

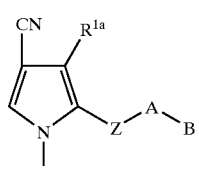

Ia

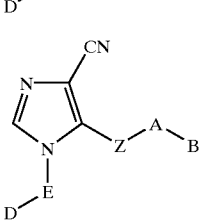

Ib

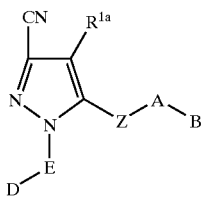

Ic

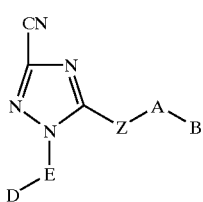

Id or pharmaceutically acceptable salt or prodrug forms thereof, wherein A, B, D, E, $R^{1a}$, and Z are defined below, are factor Xa inhibitors.

DETAILED DESCRIPTION OF PREFERRED EMBODIMENTS

Thus, in an embodiment, the present invention provides novel compounds of formulae Ia, Ib, Ic, and Id:

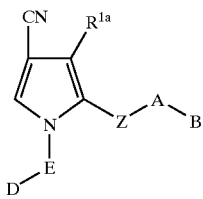

Ia

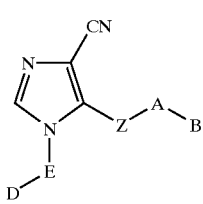

Ib

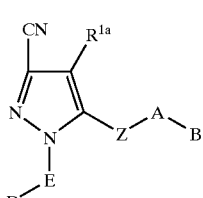

Ic

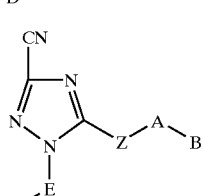

Id or a stereoisomer or pharmaceutically acceptable salt thereof, wherein;

D is selected from $C(=NR^2)NR^7R^9$, $C(O)NR^7R^8$, $NR^7R^8$, and $CH_2NR^7R^8$, provided that D is substituted meta or para to ring M on E;

E is phenyl substituted with 1 R or pyridyl substituted with 1 R;

R is selected from H, Cl, F, $OR^3$, $CH_3$, $CH_2CH_3$, $OCF_3$, and $CF_3$;

Z is selected from C(O), $CH_2C(O)$, $C(O)CH_2$, NHC(O), and C(O)NH, provided that Z does not form a N—N bond with group A;

$R^{1a}$ is selected from H, $-(CH_2)_r-R^{1'}$, $-CH=CH-R^{1'}$, $NCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$;

$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $CH(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2$— residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$; alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:
$C_{3-10}$ carbocyclic residue substituted with 0–2 $R^4$, and 5–10 membered heterocyclic system containing from 1–4 heteroatoms selected from the group consisting of N, O, and S substituted with 0–2 $R^4$;

B is selected from:
X—Y, $NR^2R^{2a}$, $C(=NR^2)NR^2R^{2a}$, $NR^2C(=NR^2)NR^2R^{2a}$, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

X is selected from $C_{1-4}$ alkylene, —$CR^2(CR^2R^{2b})$ $(CH_2)_t$—, —C(O)—, —C(=NR$^{1''}$)—, —$CR^2$ (NR$^{1''}$R$^2$)—, —$CR^2(OR^2)$—, —$CR^2(SR^2)$—, —C(O) $CR^2R^{2a}$—, —$CR^2R^{2a}C(O)$, —S(O)$_p$—, —S(O)$_p$ $CR^2R^{2a}$—, —$CR^2R^{2a}S(O)_p$—, —S(O)$_2$NR$^2$—, —NR$^2$S(O)$_2$—, —NR$^2$S(O)$_2$CR$^2$R$^{2a}$—, —CR$^2$R$^{2a}$S (O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O) CR$^2$R$^{2a}$—, —CR$^2$R$^{2a}$C(O)NR$^2$—, —CR$^2$R$^{2a}$NR$^2$C (O)—, —NR$^2$C(O)O—, —OC(O)NR$^2$—, —NR$^2$C(O) NR$^2$—, —NR$^2$—, —NR$^2$CR$^2$R$^{2a}$—, —CR$^2$R$^{2a}$NR$^2$—, O, —CR$^2$R$^{2a}$C—, and —OCR$^2$R$^{2a}$—;

Y is selected from:
  $(CH_2)_rNR^2R^{2a}$, provided that X—Y do not form a N—N, O—N, or S—N bond,
  $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_r$ OR$^2$, F, Cl, Br, I, $C_{1-4}$ alkyl, —CN, NO$_2$, $(CH_2)_r$ NR$^2$R$^{2a}$, $(CH_2)_rC(O)R^{2c}$, NR$^2$C(O)R$^{2b}$, C(O)NR$^2$R$^{2a}$, NR$^2$C(O)NR$^2$R$^{2a}$, CH(=NR$^2$)NR$^2$R$^{2a}$, CH(=NS(O)$_2$ R$^5$)NR$^2$R$^{2a}$, NHC(=NR$^2$)NR$^2$R$^{2a}$, C(O)NHC(=NR$^2$) NR$^2$R$^{2a}$, SO$_2$NR$^2$R$^{2a}$, NR$^2$SO$_2$NR$^2$R$^{2a}$, NR$^2$SO$_2$— $C_{1-4}$ alkyl, NR$^2$SO$_2$R$^5$, S(O)$_p$R$^5$, (CF$_2$)$_r$ CF$_3$, NCH$_2$R$^{1''}$, OCH$_2$R$^{1''}$, SCH$_2$R$^{1''}$, N(CH$_2$)$_2$(CH$_2$)$_t$ R$^{1''}$, $(CH_2)_2(CH_2)_tR^{1''}$, and S(CH$_2$)$_2$(CH$_2$)$_tR^{1''}$;

alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_r$ OR$^2$, $(CH_2)_r$—F, $(CH_2)_r$—Br, $(CH_2)_r$—Cl, Cl, Br, F, I, $C_{1-4}$ alkyl, —CN, NO$_2$, $(CH_2)_rNR^2R^{2a}$, $(CH_2)_rC(O)$ R$^{2c}$, NR$^2$C(O)R$^{2b}$, C(O)NR$^2$R$^{2a}$, C(O)NH(CH$_2$)$_2$ NR$^2$R$^{2a}$, NR$^2$C(O)NR$^2$R$^{2a}$, CH(=NR$^2$)NR$^2$R$^{2a}$, NHC (=NR$^2$)NR$^2$R$^{2a}$, SO$_2$NR$^2$R$^{2a}$, NR$^2$SO$_2$NR$^2$R$^{2a}$, NR$^2$SO$_2$—$C_{1-4}$ alkyl, C(O)NHSO$_2$—$C_{1-4}$ alkyl, NR$^2$SO$_2$R$^5$, S(O)$_p$R$^5$, and (CF$_2$)$_r$CF$_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_r$ OR$^3$, F, Cl, Br, I, $C_{1-4}$ alkyl, —CN, NO$_2$, $(CH_2)_r$ NR$^3$R$^{3a}$, $(CH_2)_rC(O)R^3$, $(CH_2)_rC(O)OR^{3c}$, NR$^3$C(O) R$^{3a}$, C(O)NR$^3$R$^{3a}$, NR$^3$C(O)NR$^3$R$^{3a}$, CH(=NR$^3$) NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—$C_{1-4}$ alkyl, NR$^3$SO$_2$CF$_3$, NR$^3$SO$_2$-phenyl, S(O)$_p$CF$_3$, S(O)$_p$—$C_{1-4}$ alkyl, S(O)$_p$-phenyl, and (CF$_2$)$_r$CF$_3$;

$R^5$, at each occurrence, is selected from CF$_3$, $C_{1-6}$ alkyl, phenyl substituted with 0–2 $R^6$, and benzyl substituted with 0–2 $R^6$;

$R^6$, at each occurrence, is selected from H, OH, $(CH_2)_r$ OR$^2$, halo, $C_{1-4}$ alkyl, —CN, NO$_2$, $(CH_2)_rNR^2R^{2a}$, $(CH_2)_rC(O)R^{2b}$, NR$^2$C(O)R$^{2b}$, NR$^2$C(O)NR$^2$R$^{2a}$, CH(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–3 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2; and,
t, at each occurrence, is selected from 0, 1, 2, and 3.

In another embodiment, the present invention provides a compound of formula Ic or Id, wherein:

A is selected from one of the following carbocyclic and heterocyclic systems which are substituted with 0–2 $R^4$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: H, Y, X—Y;

X is selected from $C_{1-4}$ alkylene, —C(O)—, —C(=NR)—, —CR$^2$(NR$^2$R$^{2a}$)—, —C(O)CR$^2$R$^{2a}$—, CR$^2$R$^{2a}$C(O), —C(O)NR$^2$—, —NR$^2$C(O)—, —C(O) NR$^2$CR$^2$R$^{2a}$—, —NR$^2$C(O)CR$^2$R$^{2a}$—, —CR$^2$R$^{2a}$C (O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is NR$^2$R$^{2a}$, provided that X—Y do not form a N—N or O—N bond;

alternatively, Y is selected from one of the following carbocyclic and heterocyclic systems which are substituted with 0–2 $R^{4a}$;
  cylcoproyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazoyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl r systems:

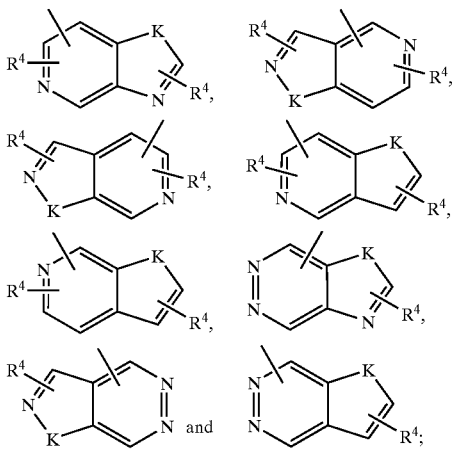

K is selected from O, S, NH, and N; and,
s is 0.

In another embodiment, the present invention provide a novel compound wherein;

E is phenyl substituted with R or 2-pyridyl substituted with R;

R is selected from H, Cl, F, OCH$_3$, CH$_3$, OCF$_3$, and CF$_3$;

Z is selected from a C(O)CH$_2$ and C(O)NH, provided that Z does not form a N—N bond with group A;

R$^{1a}$ is selected from H, CH$_3$, CH$_2$CH$_3$, Cl, F, CF$_3$, OCH$_3$, NR$^2$R$^{2a}$, S(O)$_p$R$^{2b}$, CH$_2$S(O)$_p$R$^{2b}$, CH$_2$NR$^2$S(O)$_p$R$^{2b}$, C(O)R$^{2c}$, CH$_2$C(O)R$^{2c}$, C(O)NR$^2$R$^{2a}$, and SO$_2$NR$^2$R$^{2a}$;

A is selected from phenyl, pyridyl, and pyrimidyl, and is substituted with 0–2 R$^4$; and, B is selected from X—Y, phenyl, pyrrolidino, morpholino, 1,2,3-triazolyl, and imidazolyl, and is substituted with 0–1 R$^{4a}$;

R$^2$, at each occurrence, is selected from H, CH$_3$, CH$_2$CH$_3$, cyclopropylmethyl, cyclobutyl, and cyclopentyl;

R$^{2a}$, at each occurrence, is H or CH$_3$;

alternatively, R$^2$ and R$^{2a}$, together with the atom to which they are attached, combine to form pyrrolidine substituted with 0–2 R$^{4b}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, (CH$_2$)$_r$OR$^2$, (CH$_2$)$_r$NR$^2$R$^{2a}$, S(O)$_p$R$^5$, SO$_2$NR$^2$R$^{2a}$, and 1-CF$_3$-tetrazol-2-yl;

R$^{4b}$, at each occurrence, is selected from H, CH$_3$, and OH;

R$^5$, at each occurrence, is selected from CF$_3$, C$_{1-6}$ alkyl, phenyl, and benzyl;

X is CH$_2$ or C(O);

Y is selected from pyrrolidino and morpholino; and, r, at each occurrence, is selected from 0, 1, and 2.

In another embodiment, the present invention provides a novel compound wherein;

R$^{1a}$ is absent or is selected from H, CH$_3$, CH$_2$CH$_3$, Cl, F, CF$_3$, OCH$_3$, NR$^2$R$^{2a}$, S(O)$_p$R$^{2a}$, C(O)NR$^2$R$^{2a}$, CH$_2$S(O)$_p$R$^{2b}$, CH$_2$NR$^2$S(O)$_p$R$^{2b}$, C(O)R$^{2c}$, CH$_2$C(O)R$^{2c}$, and SO$_2$NR$^2$R$^{2a}$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl) phenyl, 2-(N-(cyclobutyl)aminomethyl)phenyl, 2-(N-(cyclopentyl)aminomethyl)phenyl, and 2-(N-(3-hydroxypyrrolidinyl)methyl)phenyl.

In another embodiment, the present invention provides a novel compound selected from the group:

1-(3-(aminomethyl)phenyl)-3-cyano-1H-pyrazole-5-(N-(2'-aminosulfonyl-[1,1']-biphen-4-yl))carboxyamide;

1-(3-(aminomethyl)phenyl)-3-cyano-1H-pyrazole-5-(N-(2'-methylsulfonyl-[1,1']-biphen-4-yl))carboxyamide;

1-(3-(aminomethyl)phenyl)-3-cyano-1H-pyrazole-5-(N-(2'-methylaminosulfonyl-[1,1']-biphen-4-yl))carboxyamide;

1-(3-(aminomethyl)phenyl)-3-cyano-1H-pyrazole-5-(N-(2'-N,N-dimethylaminosulfonyl-[1,1']-biphen-4-yl)) carboxyamide;

1-(3-(aminomethyl)phenyl)-3-cyano-1H-pyrazole-5-(N-(2'-N-pyrrolidinomethyl-[1,1']-biphen-4-yl))carboxyamide;

1-(3-(aminomethyl)phenyl)-3-cyano-1H-pyrazole-5-(N-(2'-N-(3"-hydroxypyrrolidino)methyl-[1,1']-biphen-4-yl)) carboxyamide;

1-(3-(aminomethyl)phenyl)-3-cyano-1H-pyrazole-5-(N-(2'-aminosulfonyl-2-fluoro-[1,1']-biphen-4-yl)) carboxyamide;

1-(3-(aminomethyl)phenyl)-3-cyano-1H-pyrazole-5-(N-(2'-methylsulfonyl-2-fluoro-[1,1']-biphen-4-yl)) carboxyamide;

1-(3-(aminomethyl)phenyl)-3-cyano-1H-pyrazole-5-(N-(2'-methylaminosulfonyl-2-fluoro-[1,1']-biphen-4-yl)) carboxyamide;

1-(3-(aminomethyl)phenyl)-3-cyano-1H-pyrazole-5-(N-(2'-N,N-dimethylaminosulfonyl-2-fluoro-[1,1']-biphen-4-yl))carboxyamide;

1-(3-(aminomethyl)phenyl)-3-cyano-1H-pyrazole-5-(N-(2-fluoro-2'-N-pyrrolidinomethyl-[1,1']-biphen-4-yl)) carboxyamide;

1-(3-(aminomethyl)phenyl)-3-cyano-1H-pyrazole-5-(N-(2-fluoro-2'-N-(3"-hydroxypyrrolidino)methyl-[1,1']-biphen-4-yl))carboxyamide;

1-(3-(aminomethyl)phenyl)-3-cyano-1H-pyrazole-5-(N-(4'-(pyrrolidinocarbonyl)phenyl))carboxyamide;

1-(3-(aminomethyl)phenyl)-3-cyano-1H-pyrazole-5-(N-(4'-(1"-methylimidazol-2"-yl)phenyl))carboxyamide;

1-(3-(aminomethyl)phenyl)-3-cyano-1H-pyrazole-5-(N-(4'-(2"-methylimidazolyl)phenyl))carboxyamide;

1-(3-(aminomethyl)phenyl)-3-cyano-1H-pyrazole-5-(N-(4'-(2"-(N,N-dimethylamino)imidazolyl)phenyl)) carboxyamide;

1-(3-(aminomethyl)phenyl)-3-cyano-1H-pyrazole-5-(N-(2'-fluoro-4'-(pyrrolidinocarbonyl)phenyl))carboxyamide;

1-(3-(aminomethyl)phenyl)-3-cyano-1H-pyrazole-5-(N-(2'-fluoro-4'-(1"-methylimidazol-2"-yl)phenyl)) carboxyamide;

1-(3-(aminomethyl)phenyl)-3-cyano-1H-pyrazole-5-(N-(2'-fluoro-4'-(2"-methylimidazolyl)phenyl))carboxyamide; and, 1-(3-(aminomethyl)phenyl)-3-cyano-1H-pyrazole-5-(N-(2'-fluoro-4'-(2"-(N,N-dimethylamino)imidazolyl)phenyl)) carboxyamide;

or a pharmaceutically acceptable salt form thereof.

In another embodiment, the present invention provides novel pharmaceutical compositions, comprising: a pharmaceutically acceptable carrier and a therapeutically effective amount of a compound of formula (I) or a pharmaceutically acceptable salt form thereof.

In another embodiment, the present invention provides a novel method for treating or preventing a thromboembolic disorder, comprising: administering to a patient in need thereof a therapeutically effective amount of a compound of formula (I) or a pharmaceutically acceptable salt form thereof.

In another embodiment, the present invention provides novel bicyclic compounds as described above for use in therapy.

In another embodiment, the present invention provides the use of novel bicyclic compounds as described above for the manufacture of a medicament for the treatment of a thromboembolic disorder.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. Alkenyl" is intended to include hydrocarbon chains of either a straight or branched configuration and one or more unsaturated carbon-carbon bonds which may occur in any stable point along the chain, such as ethenyl and propenyl. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl and propynyl. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benztriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Preferred prodrugs are amidine prodrugs wherein D is C(=$NR^7$)$NH_2$ or its tautomer C(=NH)$NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit factor Xa. The combination of compounds is preferably a synergistic combination. Synergy, as described for example by Chou and Talalay, *Adv. Enzyme Regul.* 1984, 22, 27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991). All references cited herein are hereby incorporated in their entirety herein by reference.

The cyano-substituted compounds of the present invention can be prepared as described in Scheme 1 (wherein D in D—E—NHNH$_2$ is a cyano group).

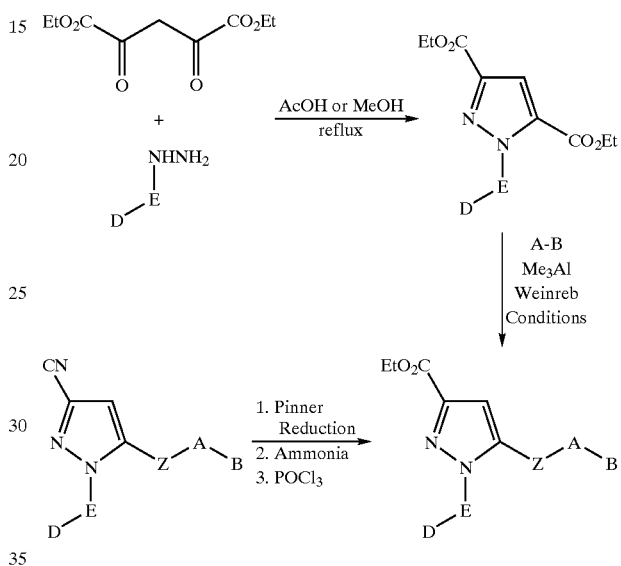

The cyano-substituted compounds of the present invention can also be prepared as described in Scheme 2 (wherein D in D—E—NHNH$_2$ is a cyano group).

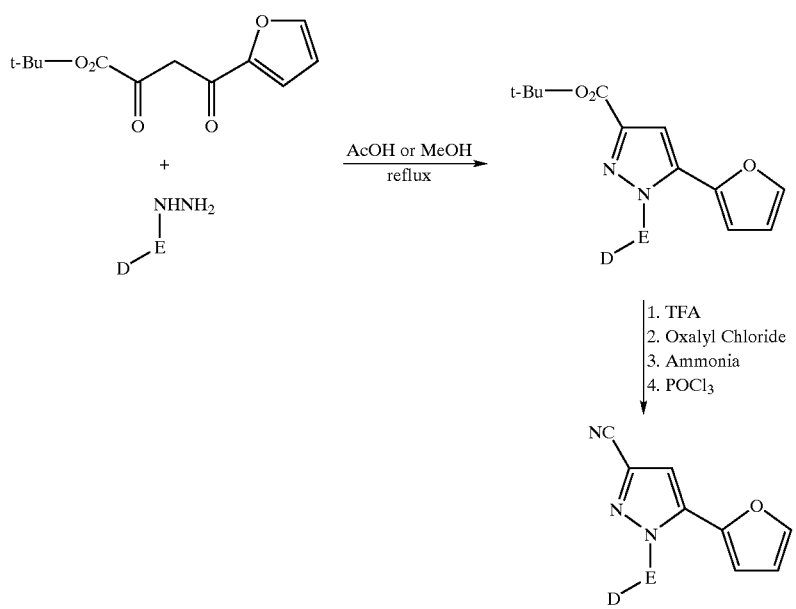

3-Cyano-1,2,4-triazoles of the present invention can be prepared from their corresponding 3-alkoxycarbonyl-1,2,4-triazoles by modifying the alkoxy carbonyl group as shown in Schemes 1 and 2. 3-Alkoxycarbonyl-1,2,4-triazoles can be prepared as shown in Scheme 29 in WO98/28269.

The compounds of the present invention have a group "A—B". Preparations of the "A—B" moieties can follow the same methods described in U.S. Pat. Nos. 5,886,191, 5,925,635, WO97/23212, WO97/30971, WO98/06694, WO98/28269, WO98/28282, WO98/57934, WO98/57937, WO98/57951, WO99/12903, and WO99/32454; the contents of which are incorporated herein by reference.

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA that was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10\ \mu M$. Preferred compounds of the present invention have $K_i$'s of $\leq 1\ \mu M$. More preferred compounds of the present invention have $K_i$'s of $\leq 0.1\ \mu M$. Even more preferred compounds of the present invention have $K_i$'s of $\leq 0.01\ \mu M$. Still more preferred compounds of the present invention have $K_i$'s of $\leq 0.001\ \mu M$.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose that produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention can be shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and EP 293 881 A2, the disclosures of which are hereby incorporated herein by reference. Other suitable boroarginine derivatives and boropeptide thrombin inhibitors include those disclosed in WO92/07869 and EP 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are given for illustration of the invention and are not intended to be limiting thereof.

The following tables contain representative examples of the present invention. Each entry in the table is to be paired with each formula at the start of the table. For example, example 1 in Table 1 is to be paired with each of the formulae of Table 1.

TABLE 1

| Ex # | $R^{1a}$ | B |
|---|---|---|
| 1. | H | 2-(aminosulfonyl)phenyl |
| 2. | H | 2-(methylaminosulfonyl)phenyl |
| 3. | H | 1-pyrrolidinocarbonyl |
| 4. | H | 2-(methylsulfonyl)phenyl |
| 5. | H | 2-(N,N-dimethylaminomethyl)phenyl |
| 6. | H | 2-(N-pyrrolidinylmethyl)phenyl |
| 7. | H | 1-methyl-2-imidazolyl |
| 8. | H | 2-methyl-1-imidazolyl |
| 9. | H | 2-(dimethylaminomethyl)-1-imidazolyl |
| 10. | H | 2-(N-(cyclopropyl-methyl)aminomethyl)phenyl |
| 11. | H | 2-(N-(cyclobutyl)-aminomethyl)phenyl |
| 12. | H | 2-(N-(cyclopentyl)-aminomethyl)phenyl |
| 13. | H | 2-(N-(3-hydroxypyrrolidinyl)-methyl)phenyl |
| 14. | H | 2-(isopropylaminomethyl)phenyl |
| 15. | H | 4-azabenzimidazol-1-yl |
| 16. | H | 5-azabenzimidazol-1-yl |
| 17. | H | 6-azabenzimidazol-1-yl |
| 18. | H | 7-azabenzimidazol-1-yl |
| 19. | CH3 | 2-(aminosulfonyl)phenyl |
| 20. | CH3 | 2-(methylaminosulfonyl)phenyl |
| 21. | CH3 | 1-pyrrolidinocarbonyl |
| 22. | CH3 | 2-(methylsulfonyl)phenyl |
| 23. | CH3 | 2-(N,N-dimethylaminomethyl)phenyl |
| 24. | CH3 | 2-(N-pyrrolidinylmethyl)phenyl |
| 25. | CH3 | 1-methyl-2-imidazolyl |
| 26. | CH3 | 2-methyl-1-imidazolyl |
| 27. | CH3 | 2-(dimethylaminomethyl)-1-imidazolyl |
| 28. | CH3 | 2-(N-(cyclopropyl-methyl)aminomethyl)phenyl |
| 29. | CH3 | 2-(N-(cyclobutyl)-aminomethyl)phenyl |
| 30. | CH3 | 2-(N-(cyclopentyl)-aminomethyl)phenyl |
| 31. | CH3 | 2-(N-(3-hydroxypyrrolidinyl)-methyl)phenyl |

TABLE 1-continued

| | | |
|---|---|---|
| 32. | CH3 | 2-(isopropylaminomethyl)phenyl |
| 33. | CH3 | 4-azabenzimidazol-1-yl |
| 34. | CH3 | 5-azabenzimidazol-1-yl |
| 35. | CH3 | 6-azabenzimidazol-1-yl |
| 36. | CH3 | 7-azabenzimidazol-1-yl |
| 37. | CH2CH3 | 2-(aminosulfonyl)phenyl |
| 38. | CH2CH3 | 2-(methylaminosulfonyl)phenyl |
| 39. | CH2CH3 | 1-pyrrolidinocarbonyl |
| 40. | CH2CH3 | 2-(methylsulfonyl)phenyl |
| 41. | CH2CH3 | 2-(N,N-dimethylaminomethyl)phenyl |
| 42. | CH2CH3 | 2-(N-pyrrolidinylmethyl)phenyl |
| 43. | CH2CH3 | 1-methyl-2-imidazolyl |
| 44. | CH2CH3 | 2-methyl-1-imidazolyl |
| 45. | CH2CH3 | 2-(dimethylaminomethyl)-1-imidazolyl |
| 46. | CH2CH3 | 2-(N-(cyclopropyl-methyl)aminomethyl)phenyl |
| 47. | CH2CH3 | 2-(N-(cyclobutyl)-aminomethyl)phenyl |
| 48. | CH2CH3 | 2-(N-(cyclopentyl)-aminomethyl)phenyl |
| 49. | CH2CH3 | 2-(N-(3-hydroxypyrrolidinyl)-methyl)phenyl |
| 50. | CH2CH3 | 2-(isopropylaminomethyl)phenyl |
| 51. | CH2CH3 | 4-azabenzimidazol-1-yl |
| 52. | CH2CH3 | 5-azabenzimidazol-1-yl |
| 53. | CH2CH3 | 6-azabenzimidazol-1-yl |
| 54. | CH2CH3 | 7-azabenzimidazol-1-yl |
| 55. | CF3 | 2-(aminosulfonyl)phenyl |
| 56. | CF3 | 2-(methylaminosulfonyl)phenyl |
| 57. | CF3 | 1-pyrrolidinocarbonyl |
| 58. | CF3 | 2-(methylsulfonyl)phenyl |
| 59. | CF3 | 2-(N,N-dimethylaminomethyl)phenyl |
| 60. | CF3 | 2-(N-pyrrolidinylmethyl)phenyl |
| 61. | CF3 | 1-methyl-2-imidazolyl |
| 62. | CF3 | 2-methyl-1-imidazolyl |
| 63. | CF3 | 2-(dimethylaminomethyl)-1-imidazolyl |
| 64. | CF3 | 2-(N-(cyclopropyl-methyl)aminomethyl)phenyl |
| 65. | CF3 | 2-(N-(cyclobutyl)-aminomethyl)phenyl |
| 66. | CF3 | 2-(N-(cyclopentyl)-aminomethyl)phenyl |
| 67. | CF3 | 2-(N-(3-hydroxypyrrolidinyl)-methyl)phenyl |
| 68. | CF3 | 2-(isopropylaminomethyl)phenyl |
| 69. | CF3 | 4-azabenzimidazol-1-yl |
| 70. | CF3 | 5-azabenzimidazol-1-yl |
| 71. | CF3 | 6-azabenzimidazol-1-yl |
| 72. | CF3 | 7-azabenzimidazol-1-yl |
| 73. | SCH3 | 2-(aminosulfonyl)phenyl |
| 74. | SCH3 | 2-(methylaminosulfonyl)phenyl |
| 75. | SCH3 | 1-pyrrolidinocarbonyl |
| 76. | SCH3 | 2-(methylsulfonyl)phenyl |
| 77. | SCH3 | 2-(N,N-dimethylaminomethyl)phenyl |
| 78. | SCH3 | 2-(N-pyrrolidinylmethyl)phenyl |
| 79. | SCH3 | 1-methyl-2-imidazolyl |
| 80. | SCH3 | 2-methyl-1-imidazolyl |
| 81. | SCH3 | 2-(dimethylaminomethyl)-1-imidazolyl |
| 82. | SCH3 | 2-(N-(cyclopropyl-methyl)aminomethyl)phenyl |
| 83. | SCH3 | 2-(N-(cyclobutyl)-aminomethyl)phenyl |
| 84. | SCH3 | 2-(N-(cyclopentyl)-aminomethyl)phenyl |
| 85. | SCH3 | 2-(N-(3-hydroxypyrrolidinyl)-methyl)phenyl |
| 86. | SCH3 | 2-(isopropylaminomethyl)phenyl |
| 87. | SCH3 | 4-azabenzimidazol-1-yl |
| 88. | SCH3 | 5-azabenzimidazol-1-yl |
| 89. | SCH3 | 6-azabenzimidazol-1-yl |
| 90. | SCH3 | 7-azabenzimidazol-1-yl |
| 91. | SOCH3 | 2-(aminosulfonyl)phenyl |
| 92. | SOCH3 | 2-(methylaminosulfonyl)phenyl |
| 93. | SOCH3 | 1-pyrrolidinocarbonyl |
| 94. | SOCH3 | 2-(methylsulfonyl)phenyl |
| 95. | SOCH3 | 2-(N,N-dimethylaminomethyl)phenyl |
| 96. | SOCH3 | 2-(N-pyrrolidinylmethyl)phenyl |
| 97. | SOCH3 | 1-methyl-2-imidazolyl |
| 98. | SOCH3 | 2-methyl-1-imidazolyl |
| 99. | SOCH3 | 2-(dimethylaminomethyl)-1-imidazolyl |
| 100. | SOCH3 | 2-(N-(cyclopropyl-methyl)aminomethyl)phenyl |
| 101. | SOCH3 | 2-(N-(cyclobutyl)-aminomethyl)phenyl |
| 102. | SOCH3 | 2-(N-(cyclopentyl)-aminomethyl)phenyl |
| 103. | SOCH3 | 2-(N-(3-hydroxypyrrolidinyl)-methyl)phenyl |
| 104. | SOCH3 | 2-(isopropylaminomethyl)phenyl |
| 105. | SOCH3 | 4-azabenzimidazol-1-yl |
| 106. | SOCH3 | 5-azabenzimidazol-1-yl |
| 107. | SOCH3 | 6-azabenzimidazol-1-yl |
| 108. | SOCH3 | 7-azabenzimidazol-1-yl |
| 109. | SO2CH3 | 2-(aminosulfonyl)phenyl |
| 110. | SO2CH3 | 2-(methylaminosulfonyl)phenyl |
| 111. | SO2CH3 | 1-pyrrolidinocarbonyl |
| 112. | SO2CH3 | 2-(methylsulfonyl)phenyl |
| 113. | SO2CH3 | 2-(N,N-dimethylaminomethyl)phenyl |
| 114. | SO2CH3 | 2-(N-pyrrolidinylmethyl)phenyl |
| 115. | SO2CH3 | 1-methyl-2-imidazolyl |
| 116. | SO2CH3 | 2-methyl-1-imidazolyl |
| 117. | SO2CH3 | 2-(dimethylaminomethyl)-1-imidazolyl |
| 118. | SO2CH3 | 2-(N-(cyclopropyl-methyl)aminomethyl)phenyl |
| 119. | SO2CH3 | 2-(N-(cyclobutyl)-aminomethyl)phenyl |
| 120. | SO2CH3 | 2-(N-(cyclopentyl)-aminomethyl)phenyl |
| 121. | SO2CH3 | 2-(N-(3-hydroxypyrrolidinyl)-methyl)phenyl |
| 122. | SO2CH3 | 2-(isopropylaminomethyl)phenyl |
| 123. | SO2CH3 | 4-azabenzimidazol-1-yl |
| 124. | SO2CH3 | 5-azabenzimidazol-1-yl |
| 125. | SO2CH3 | 6-azabenzimidazol-1-yl |
| 126. | SO2CH3 | 7-azabenzimidazol-1-yl |
| 127. | Cl | 2-(aminosulfonyl)phenyl |
| 128. | Cl | 2-(methylaminosulfonyl)phenyl |
| 129. | Cl | 1-pyrrolidinocarbonyl |
| 130. | Cl | 2-(methylsulfonyl)phenyl |
| 131. | Cl | 2-(N,N-dimethylaminomethyl)phenyl |
| 132. | Cl | 2-(N-pyrrolidinylmethyl)phenyl |
| 133. | Cl | 1-methyl-2-imidazolyl |
| 134. | Cl | 2-methyl-1-imidazolyl |
| 135. | Cl | 2-(dimethylaminomethyl)-1-imidazolyl |
| 136. | Cl | 2-(N-(cyclopropyl-methyl)aminomethyl)phenyl |
| 137. | Cl | 2-(N-(cyclobutyl)-aminomethyl)phenyl |
| 138. | Cl | 2-(N-(cyclopentyl)-aminomethyl)phenyl |
| 139. | Cl | 2-(N-(3-hydroxypyrrolidinyl)-methyl)phenyl |
| 140. | Cl | 2-(isopropylaminomethyl)phenyl |
| 141. | Cl | 4-azabenzimidazol-1-yl |
| 142. | Cl | 5-azabenzimidazol-1-yl |
| 143. | Cl | 6-azabenzimidazol-1-yl |
| 144. | Cl | 7-azabenzimidazol-1-yl |
| 145. | F | 2-(aminosulfonyl)phenyl |
| 146. | F | 2-(methylaminosulfonyl)phenyl |
| 147. | F | 1-pyrrolidinocarbonyl |
| 148. | F | 2-(methylsulfonyl)phenyl |
| 149. | F | 2-(N,N-dimethylaminomethyl)phenyl |
| 150. | F | 2-(N-pyrrolidinylmethyl)phenyl |
| 151. | F | 1-methyl-2-imidazolyl |
| 152. | F | 2-methyl-1-imidazolyl |
| 153. | F | 2-(dimethylaminomethyl)-1-imidazolyl |
| 154. | F | 2-(N-(cyclopropyl-methyl)aminomethyl)phenyl |
| 155. | F | 2-(N-(cyclobutyl)-aminomethyl)phenyl |
| 156. | F | 2-(N-(cyclopentyl)-aminomethyl)phenyl |
| 157. | F | 2-(N-(3-hydroxypyrrolidinyl)-methyl)phenyl |
| 158. | F | 2-(isopropylaminomethyl)phenyl |
| 159. | F | 4-azabenzimidazol-1-yl |
| 160. | F | 5-azabenzimidazol-1-yl |
| 161. | F | 6-azabenzimidazol-1-yl |
| 162. | F | 7-azabenzimidazol-1-yl |
| 163. | CO2CH3 | 2-(N-pyrrolidinylmethyl)phenyl |
| 164. | CO2CH3 | 1-methyl-2-imidazolyl |
| 165. | CO2CH3 | 2-methyl-1-imidazolyl |
| 166. | CO2CH3 | 2-(dimethylaminomethyl)-1-imidazolyl |
| 167. | CO2CH3 | 2-(N-(cyclopropyl-methyl)aminomethyl)phenyl |
| 168. | CO2CH3 | 2-(N-(cyclobutyl)-aminomethyl)phenyl |
| 169. | CO2CH3 | 2-(N-(cyclopentyl)-aminomethyl)phenyl |
| 170. | CO2CH3 | 2-(N-(3-hydroxypyrrolidinyl)-methyl)phenyl |
| 171. | CO2CH3 | 2-(isopropylaminomethyl)phenyl |
| 172. | CO2CH3 | 4-azabenzimidazol-1-yl |
| 173. | CO2CH3 | 5-azabenzimidazol-1-yl |
| 174. | CO2CH3 | 6-azabenzimidazol-1-yl |
| 175. | CO2CH3 | 7-azabenzimidazol-1-yl |
| 176. | CH2OCH3 | 2-(aminosulfonyl)phenyl |
| 177. | CH2OCH3 | 2-(methylaminosulfonyl)phenyl |
| 178. | CH2OCH3 | 1-pyrrolidinocarbonyl |
| 179. | CH2OCH3 | 2-(methylsulfonyl)phenyl |
| 180. | CH2OCH3 | 2-(N,N-dimethylaminomethyl)phenyl |
| 181. | CH2OCH3 | 2-(N-pyrrolidinylmethyl)phenyl |
| 182. | CH2OCH3 | 1-methyl-2-imidazolyl |
| 183. | CH2OCH3 | 2-methyl-1-imidazolyl |
| 184. | CH2OCH3 | 2-(dimethylaminomethyl)-1-imidazolyl |
| 185. | CH2OCH3 | 2-(N-(cyclopropyl-methyl)aminomethyl)phenyl |
| 186. | CH2OCH3 | 2-(N-(cyclobutyl)-aminomethyl)phenyl |
| 187. | CH2OCH3 | 2-(N-(cyclopentyl)-aminomethyl)phenyl |
| 188. | CH2OCH3 | 2-(N-(3-hydroxypyrrolidinyl)-methyl)phenyl |
| 189. | CH2OCH3 | 2-(isopropylaminomethyl)phenyl |

TABLE 1-continued

| | | |
|---|---|---|
| 190. | CH2OCH3 | 4-azabenzimidazol-1-yl |
| 191. | CH2OCH3 | 5-azabenzimidazol-1-yl |
| 192. | CH2OCH3 | 6-azabenzimidazol-1-yl |
| 193. | CH2OCH3 | 7-azabenzimidazol-1-yl |
| 194. | CONH2 | 2-(aminosulfonyl)phenyl |
| 195. | CONH2 | 2-(methylaminosulfonyl)phenyl |
| 196. | CONH2 | 1-pyrrolidinocarbonyl |
| 197. | CONH2 | 2-(methylsulfonyl)phenyl |
| 198. | CONH2 | 2-(N,N-dimethylaminomethyl)phenyl |
| 199. | CONH2 | 2-(N-pyrrolidinylmethyl)phenyl |
| 200. | CONH2 | 1-methyl-2-imidazolyl |
| 201. | CONH2 | 2-methyl-1-imidazolyl |
| 202. | CONH2 | 2-(dimethylaminomethyl)-1-imidazolyl |
| 203. | CONH2 | 2-(N-(cyclopropyl-methyl)aminomethyl)phenyl |
| 204. | CONH2 | 2-(N-(cyclobutyl)-aminomethyl)phenyl |
| 205. | CONH2 | 2-(N-(cyclopentyl)-aminomethyl)phenyl |
| 206. | CONH2 | 2-(N-(3-hydroxypyrrolidinyl)-methyl)phenyl |
| 207. | CONH2 | 2-(isopropylaminomethyl)phenyl |
| 208. | CONH2 | 4-azabenzimidazol-1-yl |
| 209. | CONH2 | 5-azabenzimidazol-1-yl |
| 210. | CONH2 | 6-azabenzimidazol-1-yl |
| 211. | CONH2 | 7-azabenzimidazol-1-yl |
| 212. | CN | 2-(aminosulfonyl)phenyl |
| 213. | CN | 2-(methylaminosulfonyl)phenyl |
| 214. | CN | 1-pyrrolidinocarbonyl |
| 215. | CN | 2-(methylsulfonyl)phenyl |
| 216. | CN | 2-(N,N-dimethylaminomethyl)phenyl |
| 217. | CN | 2-(N-pyrrolidinylmethyl)phenyl |
| 218. | CN | 1-methyl-2-imidazolyl |
| 219. | CN | 2-methyl-1-imidazolyl |
| 220. | CN | 2-(dimethylaminomethyl)-1-imidazolyl |
| 221. | CN | 2-(N-(cyclopropyl-methyl)aminomethyl)phenyl |
| 222. | CN | 2-(N-(cyclobutyl)-aminomethyl)phenyl |
| 223. | CN | 2-(N-(cyclopentyl)-aminomethyl)phenyl |
| 224. | CN | 2-(N-(3-hydroxypyrrolidinyl)-methyl)phenyl |
| 225. | CN | 2-(isopropylaminomethyl)phenyl |
| 226. | CN | 4-azabenzimidazol-1-yl |
| 227. | CN | 5-azabenzimidazol-1-yl |
| 228. | CN | 6-azabenzimidazol-1-yl |
| 229. | CN | 7-azabenzimidazol-1-yl |
| 230. | CH2NH2 | 2-(N-pyrrolidinylmethyl)phenyl |
| 231. | CH2NH2 | 1-methyl-2-imidazolyl |
| 232. | CH2NH2 | 2-methyl-1-imidazolyl |
| 233. | CH2NH2 | 2-(dimethylaminomethyl)-1-imidazolyl |
| 234. | CH2NH2 | 2-(N-(cyclopropyl-methyl)aminomethyl)phenyl |
| 235. | CH2NH2 | 2-(N-(cyclobutyl)-aminomethyl)phenyl |
| 236. | CH2NH2 | 2-(N-(cyclopentyl)-aminomethyl)phenyl |
| 237. | CH2NH2 | 2-(N-(3-hydroxypyrrolidinyl)-methyl)phenyl |
| 238. | CH2NH2 | 2-(isopropylaminomethyl)phenyl |
| 239. | CH2NH2 | 4-azabenzimidazol-1-yl |
| 240. | CH2NH2 | 5-azabenzimidazol-1-yl |
| 241. | CH2NH2 | 6-azabenzimidazol-1-yl |
| 242. | CH2NH2 | 7-azabenzimidazol-1-yl |
| 243. | CH2NHSO2CH3 | 2-(aminosulfonyl)phenyl |
| 244. | CH2NHSO2CH3 | 2-(methylaminosulfonyl)phenyl |
| 245. | CH2NHSO2CH3 | 1-pyrrolidinocarbonyl |
| 246. | CH2NHSO2CH3 | 2-(methylsulfonyl)phenyl |
| 247. | CH2NHSO2CH3 | 2-(N,N-dimethylaminomethyl)phenyl |
| 248. | CH2NHSO2CH3 | 2-(N-pyrrolidinylmethyl)phenyl |
| 249. | CH2NHSO2CH3 | 1-methyl-2-imidazolyl |
| 250. | CH2NHSO2CH3 | 2-methyl-1-imidazolyl |
| 251. | CH2NHSO2CH3 | 2-(dimethylaminomethyl)-1-imidazolyl |
| 252. | CH2NHSO2CH3 | 2-(N-(cyclopropyl-methyl)aminomethyl)phenyl |
| 253. | CH2NHSO2CH3 | 2-(N-(cyclobutyl)-aminomethyl)phenyl |
| 254. | CH2NHSO2CH3 | 2-(N-(cyclopentyl)-aminomethyl)phenyl |
| 255. | CH2NHSO2CH3 | 2-(N-(3-hydroxypyrrolidinyl)-methyl)phenyl |
| 256. | CH2NHSO2CH3 | 2-(isopropylaminomethyl)phenyl |
| 257. | CH2NHSO2CH3 | 4-azabenzimidazol-1-yl |
| 258. | CH2NHSO2CH3 | 5-azabenzimidazol-1-yl |
| 259. | CH2NHSO2CH3 | 6-azabenzimidazol-1-yl |
| 260. | CH2NHSO2CH3 | 7-azabenzimidazol-1-yl |

TABLE 2

| Ex # | B |
|---|---|
| 261. | 2-(aminosulfonyl)phenyl |
| 262. | 2-(methylaminosulfonyl)phenyl |
| 263. | 1-pyrrolidinocarbonyl |
| 264. | 2-(methylsulfonyl)phenyl |
| 265. | 2-(N,N-dimethylaminomethyl)phenyl |
| 266. | 2-(N-pyrrolidinylmethyl)phenyl |
| 267. | 1-methyl-2-imidazolyl |
| 268. | 2-methyl-1-imidazolyl |
| 269. | 2-(dimethylaminomethyl)-1-imidazolyl |
| 270. | 2-(N-(cyclopropyl-methyl)aminomethyl)phenyl |
| 271. | 2-(N-(cyclobutyl)-aminomethyl)phenyl |
| 272. | 2-(N-(cyclopentyl)-aminomethyl)phenyl |
| 273. | 2-(N-(3-hydroxypyrrolidinyl)-methyl)phenyl |
| 274. | 2-(isopropylaminomethyl)phenyl |
| 275. | 4-azabenzimidazol-1-yl |
| 276. | 5-azabenzimidazol-1-yl |
| 277. | 6-azabenzimidazol-1-yl |
| 278. | 7-azabenzimidazol-1-yl |

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula Ic:

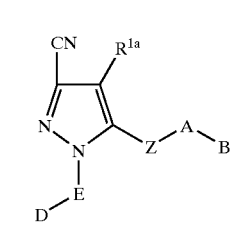

or a stereoisomer or pharmaceutically acceptable salt thereof, wherein;

D is selected from $C(=NR^8)NR^7R^9$, $C(O)NR^7R^8$, and $CH_2NR^7R^8$, provided that D is substituted meta or para to ring M on E;

E is phenyl substituted with 1 R;

R is selected from H, Cl, F, $OR^3$, $CH_3$, $CH_2CH_3$, $OCF_3$, and $CF_3$;

Z is selected from $C(O)CH_2$ and $C(O)NH$;

$R^{1a}$ is selected from H, $-(CH_2)_r-R^{1'}$, and $-CH=CH-R^{1'}$;

$R^{1'}$ is selected from H, $C_{1-3}$ alkyl, F, Cl, Br, I, $-CN$, $-CHO$, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, and $C_{3-6}$ carbocyclic residue substituted with 0–2 $R^{4a}$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2-$ residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is a $C_{3-10}$ carbocyclic residue substituted with 0–2 $R^4$;

B is selected from:
  $C_{3-10}$ carbocyclic residue substituted with 0–2 $R^{4a}$, and imidazolyl substituted with 0–2 $R^{4a}$;

$R^4$, at each occurrence, is selected from H, $=O$, $(CH_2)_rOR^2$, F, Cl, Br, I, $C_{1-4}$ alkyl, $-CN$, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)$ $NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_tR^{1'}$, $^{(CH}_2)_2(CH_2)_t$ $R^{1''}$, and $S(CH_2)_2(CH_2)_tR^{1''}$;

$R^{4a}$, at each occurrence, is selected from H, $=O$, $(CH_2)_rOR^2$, $(CH_2)_r-F$, $(CH_2)_r-Br$, $(CH_2)_r-Cl$, Cl, Br, F, I, $C_{1-4}$ alkyl, $-CN$, $NO_2$, $(CH_2)_rNR^2R^{2a}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2-C_{1-4}$ alkyl, $C(O)NHSO_2-C_{1-4}$ alkyl, $NR^2SO_2R^5$, $S(O)_pR^5$, and $(CF_2)_rCF_3$;

$R^{4b}$, at each occurrence, is selected from H, $=O$, $(CH_2)_rOR^3$, F, Cl, Br, I, $C_{1-4}$ alkyl, $-CN$, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, $-CN$, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

$R^9$, at each occurrence, is selected from H, $C_{1-6}$ alkyl and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, and 3; and, t, at each occurrence, is selected from 0, 1, 2, and 3.

2. A compound according to claim 1, wherein;

A is phenyl substituted with 0–2 $R^4$.

3. A compound according to claim 2, wherein;

R is selected from H, Cl, F, $OCH_3$, $CH_3$, $OCF_3$, and $CF_3$;

$R^{1a}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_2R^{2b}$, $C(O)R^{2c}$, $CH_2C(O)R^{2c}$, $C(O)NR^2R^{2a}$, and $SO_2NR^2R^{2a}$;

B is selected from phenyl and imidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$;

alternatively, $R^2$ and $R^{2a}$, together with the atom to which they are attached, combine to form pyrrolidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rOR^2$, $(CH_2)_rNR^2R^{2a}$, $S(O)_pR^5$, and $SO_2NR^2R^{2a}$;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

4. A compound according to claim 3, wherein;

$R^{1a}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_2R^{2b}$, $C(O)R^{2c}$, $CH_2C(O)R^{2c}$, and $SO_2NR^2R^{2a}$; and, B is selected from the group: 2-(aminosulfonyl)phenyl, 2-(methylaminosulfonyl)phenyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl) phenyl, 2-(N-(cyclobutyl)aminomethyl)phenyl, 2-(N-(cyclopentyl)aminomethyl)phenyl, and 2-(N-(3-hydroxypyrrolidinyl)methyl)phenyl.

5. A compound according to claim 1, wherein the compound is selected from the group:

1-(3-(aminomethyl)phenyl)-3-cyano-1H-pyrazole-5-(N-(2'-aminosulfonyl-[1,1']-biphen-4-yl))carboxyamide;

1-(3-(aminomethyl)phenyl)-3-cyano-1H-pyrazole-5-(N-(2'-methylsulfonyl-[1,1']-biphen-4-yl))carboxyamide;

1-(3-(aminomethyl)phenyl)-3-cyano-1H-pyrazole-5-(N-(2'-methylaminosulfonyl-[1,1']-biphen-4-yl))carboxyamide;

1-(3-(aminomethyl)phenyl)-3-cyano-1H-pyrazole-5-(N-(2'-N,N-dimethylaminosulfonyl-[1,1']-biphen-4-yl)) carboxyamide;

1-(3-(aminomethyl)phenyl)-3-cyano-1H-pyrazole-5-(N-(2'-N-pyrrolidinomethyl-[1,1']-biphen-4-yl))carboxyamide;

1-(3-(aminomethyl)phenyl)-3-cyano-1H-pyrazole-5-(N-(2'-aminosulfonyl-2-fluoro-[1,1']-biphen-4-yl)) carboxyamide;

1-(3-(aminomethyl)phenyl)-3-cyano-1H-pyrazole-5-(N-(2'-methylsulfonyl-2-fluoro-[1,1']-biphen-4-yl)) carboxyamide;

1-(3-(aminomethyl)phenyl)-3-cyano-1H-pyrazole-5-(N-(2'-methylaminosulfonyl-2-fluoro-[1,1']-biphen-4-yl)) carboxyamide;

1-(3-(aminomethyl)phenyl)-3-cyano-1H-pyrazole-5-(N-(2'-N,N-dimethylaminosulfonyl-2-fluoro-[1,1']-biphen-4-yl))carboxyamide;

1-(3-(aminomethyl)phenyl)-3-cyano-1H-pyrazole-5-(N-(2-fluoro-2'-N-pyrrolidinomethyl-[1,1']-biphen-4-yl)) carboxyamide;

1-(3-(aminomethyl)phenyl)-3-cyano-1H-pyrazole-5-(N-(2-fluoro-2'-N-(3"-hydroxypyrrolidino)methyl-[1,1']-biphen-4-yl))carboxyamide;

1-(3-(aminomethyl)phenyl)-3-cyano-1H-pyrazole-5-(N-(4'-(pyrrolidinocarbonyl)phenyl))carboxyamide;

1-(3-(aminomethyl)phenyl)-3-cyano-1H-pyrazole-5-(N-(4'-(1"-methylimidazol-2"-yl)phenyl))carboxyamide;

1-(3-(aminomethyl)phenyl)-3-cyano-1H-pyrazole-5-(N-(4'-(2"-methylimidazolyl)phenyl))carboxyamide;

1-(3-(aminomethyl)phenyl)-3-cyano-1H-pyrazole-5-(N-(4'-(2"-(N,N-dimethylamino)imidazolyl)phenyl)) carboxyamide;

1-(3-(aminomethyl)phenyl)-3-cyano-1H-pyrazole-5-(N-(2'-fluoro-4'-(pyrrolidinocarbonyl)phenyl))carboxyamide;

1-(3-(aminomethyl)phenyl)-3-cyano-1H-pyrazole-5-(N-(2'-fluoro-4'-(1"-methylimidazol-2"-yl)phenyl)) carboxyamide;

1-(3-(aminomethyl)phenyl)-3-cyano-1H-pyrazole-5-(N-(2'-fluoro-4'-(2"-methylimidazolyl)phenyl))carboxyamide; and, 1-(3-(aminomethyl)phenyl)-3-cyano-1H-pyrazole-5-(N-(2'-fluoro-4'-(2"-(N,N-dimethylamino)imidazolyl)phenyl)) carboxyamide;

or a pharmaceutically acceptable salt form thereof.

6. A pharmaceutical composition, comprising: a pharmaceutically acceptable carrier and a therapeutically effective amount of a compound of claim 1 or a pharmaceutically acceptable salt form thereof.

7. A pharmaceutical composition, comprising: a pharmaceutically acceptable carrier and a therapeutically effective amount of a compound of claim 2 or a pharmaceutically acceptable salt form thereof.

8. A pharmaceutical composition, comprising: a pharmaceutically acceptable carrier and a therapeutically effective amount of a compound of claim 3 or a pharmaceutically acceptable salt form thereof.

9. A pharmaceutical composition, comprising: a pharmaceutically acceptable carrier and a therapeutically effective amount of a compound of claim 4 or a pharmaceutically acceptable salt form thereof.

10. A pharmaceutical composition, comprising: a pharmaceutically acceptable carrier and a therapeutically effective amount of a compound of claim 5 or a pharmaceutically acceptable salt form thereof.

11. A method for treating a thromboembolic disorder, comprising: administering to a patient in need thereof a therapeutically effective amount of a compound of claim 1 or a pharmaceutically acceptable salt form thereof.

12. A method for treating a thromboembolic disorder, comprising: administering to a patient in need thereof a therapeutically effective amount of a compound of claim 2 or a pharmaceutically acceptable salt form thereof.

13. A method for treating a thromboembolic disorder, comprising: administering to a patient in need thereof a therapeutically effective amount of a compound of claim 3 or a pharmaceutically acceptable salt form thereof.

14. A method for treating a thromboembolic disorder, comprising: administering to a patient in need thereof a therapeutically effective amount of a compound of claim 4 or a pharmaceutically acceptable salt form thereof.

15. A method for treating a thromboembolic disorder, comprising: administering to a patient in need thereof a therapeutically effective amount of a compound of claim 5 or a pharmaceutically acceptable salt form thereof.

* * * * *

UNITED STATES PATENT AND TRADEMARK OFFICE
CERTIFICATE OF CORRECTION

PATENT NO.   : 6,407,256 B1
DATED         : June 18, 2002
INVENTOR(S)  : Donald J.P. Pinto It is certified that error appears in the above-identified patent and that said Letters Patent is hereby corrected as shown below:

<u>Title page,</u>
Below Item [76], and between the term notice (*) insert the following:
-- [73] Assignee: Bristol-Myers Squibb Pharma Company, Princeton, NJ (US) --.

Signed and Sealed this

Fifth Day of November, 2002

*Attest:*

*Attesting Officer*

JAMES E. ROGAN
*Director of the United States Patent and Trademark Office*